United States Patent [19]

Hofmeister et al.

[11] Patent Number: 4,939,275
[45] Date of Patent: Jul. 3, 1990

[54] PERIPLANONE A

[75] Inventors: Peter Hofmeister, Neustadt; Wolfgang Krieg, Weingarten; Reinhard Neudert, Bissersheim; Hagen Hauptmann, Regensburg, all of Fed. Rep. of Germany

[73] Assignee: BASF Aktiengesellschaft, Ludwigshafen, Fed. Rep. of Germany

[21] Appl. No.: 117,294

[22] Filed: Nov. 6, 1987

[30] Foreign Application Priority Data

Nov. 22, 1986 [DE] Fed. Rep. of Germany ....... 3639941

[51] Int. Cl.$^5$ .......................................... C07D 303/04
[52] U.S. Cl. ................................................... 549/332
[58] Field of Search .......................................... 549/332

[56] References Cited

U.S. PATENT DOCUMENTS 4,339,388 7/1982 Still ..................................... 549/332

FOREIGN PATENT DOCUMENTS

WO87/03593 6/1987 Japan ..................................... 549/332

OTHER PUBLICATIONS

Schreiber, et al., "Tetrahedron Letters," vol. 22, No. 46, 1981, pp. 4651–5654.
Hauptmann, et al., "Tetrahedron Letters," vol. 27, No. 51, 1986, pp. 6189–6192.
Shizuri, et al., "Tetrahedron Letters," vol. 28, No. 16, 1987, pp. 1791–1798.

Primary Examiner—Richard L. Raymond
Assistant Examiner—James H. Turnipseed
Attorney, Agent, or Firm—Keil & Weinkauf

[57] ABSTRACT

Synthetically prepared periplanone A of the formula I

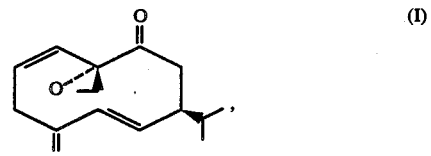

its preparation and its use for controlling cockroaches.

1 Claim, No Drawings

PERIPLANONE A

The sexual attractant of the American cockroach (*Periplaneta americana*) was discovered in 1952 (L. M. Roth and E. R. Willis, Am. Midl. Nat. 47 (1952), 66).

Work on the identification of the attractant mixture led to two biologically active compounds, which have been named periplanone A and periplanone B and have been assigned the following structures (VI) and (VII):

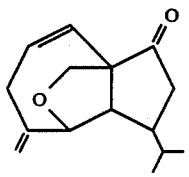
(VI)

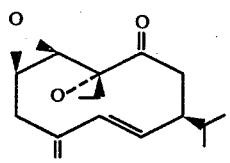
(VII)

(C. J. Persoons et al., Israel. J. Chem. 17 (1978), 227, C. J. Persoons, Thesis, Wageningen (Netherlands), 1977, C. J. Persoons et al., Tetrahedron Lett., 1976, 2056, and W. C. Still, J. Amer. Chem. Soc. 101 (1979), 2493).

In the unsuccessful attempt to synthesize VI, it was found that the presumed substance must have a different structure. Consequently, it was found that periplanone A does not possess a structure which can be described by formula VI but instead has a structure of the formula I, similar to periplanone B (formula VII)

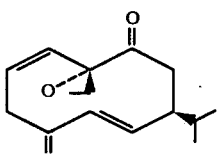
(I)

Although the synthetic active ingredient has a somewhat lower biological activity than the natural one, this is presumably due to the presence of the steric antipode. However, in view of the advantageous method of preparation for the mixture of the stereoisomers this is not disadvantageous.

The synthesis route described here for (±)-periplanone A starts from the known compound cyclodecatrienone (II) (W. C. Still, J. Amer. Chem. Soc. 101 (1979), 2493) and proceeds via the novel intermediates (III), (IV) and (V). The intermediate V is of particular interest since it can be expoxidized stereoselectively to give (±)-periplanone A in good yield; specifically, the procedure adopted is as follows:

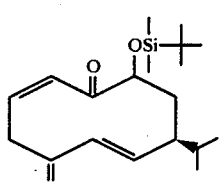
(II)

In an olefination reaction, for example using the Tebbe reagent (F. N. Tebbe, et al., J. Amer. Chem. Soc. 100 (1978), 3611), the cyclodecatetraene III is formed from (II).

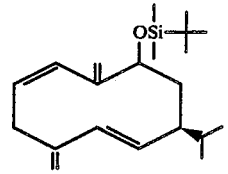
(III)

By eliminating the tert-butyldimethylsilyl radical using a conventional cleavage reagent for silyl ethers, preferably a fluoride, the alcohol (IV) is obtained; oxidation of this gives the cyclodecatetraenone (V).

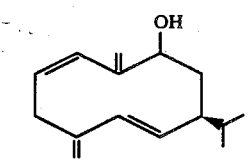
(IV)

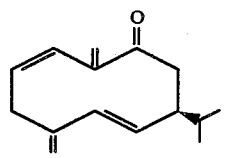
(V)

Known reagents may be used as oxidizing agents, and known methods employed. The reaction takes place with a good yield if pyridinium chlorochromate on neutral alumina is used (Y. S. Cheng et al., Synthesis, 1980, 223).

(V) can be converted to (I) with the aid of epoxidizing agents. For example, the reagent tert-butyl hydroperoxide/KH epoxidizes (V) stereoselectively at from 0° to −50° C., preferably −20° C., to give the racemate of the structure I.

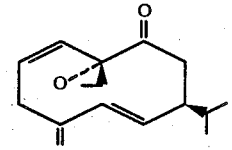
(I)

There is virtually no formation of the corresponding diastereomers.

The practical data below illustrate the process.

Preparation of compound III 255 mg (0.76 millimole) of cyclodecatrienone II, dissolved in 1 ml of tetrahydrofuran, are added to a solution of 326 mg (1.14 millimoles) of Tebbe reagent $Cp_2TiCH_2AlCl(CH_3)_2$ in 5 ml of tetrahydrofuran and 230 μl of pyridine at −40° C. After 10 minutes, the mixture is stirred for a further 40 minutes at room temperature. Thereafter, 2.2 g of 15% strength sodium hydroxide solution are added dropwise at −10° C., and the mixture is allowed to reach room temperature in the course of 15 minutes. It is diluted with diethyl ether and filtered through silica gel. After the solvent has been stripped off and the residue worked up by column chromatography over silica gel using 40/60 petroleum ether as an eluent, 113 mg (45%) of cyclodecatetraene III are isolated as a colorless oil ($R_f=0.3$).

Preparation of compound IV 4 ml of a 1 molar solution of tetrabutylammonium fluoride in tetrahydrofuran are added to a solution of 127 mg (0.38 millimole) of compound III in 1.5 ml of tetrahydrofuran at room temperature. After 20 minutes, the mixture is poured onto saturated sodium chloride solution and extracted three times by shaking with diethyl ether, and the extract is dried over sodium sulfate. After the ether has been stripped off and the residue purified by column chromatography over silica gel using 20% strength tert-butyl methyl ether in petroleum ether (40/60) as an eluent, 80 mg (96% yield) of IV are isolated as a colorless oil ($R_f=0.57$ (30% strength tert-butyl methyl ether in petroleum ether)).

Preparation of compound V 71 mg (0.33 millimole) of the alcohol IV in 10 ml of diethyl ether are stirred at room temperature with 6.0 g of pyridinium chlorochromate on neutral alumina and 1.5 g of sodium bicarbonate for 50 minutes. The concentrated filtrate is purified by column chromatography over silica gel using 10% strength tert-butyl methyl ether in petroleum ether (40/60) to give 46 mg (66% yield) of the ketone V as a colorless oil ($R_f=0.61$).

Preparation of compound I 14 mg (0.35 millimole) of potassium hydride are suspended in 4 ml of tetrahydrofuran, and 150 μl (0.45 millimole) of a 3 molar solution of tert-butyl hydroperoxide in toluene are added at 0° C. After 10 minutes, 40 mg (0.18 millimole) of the cyclodecatetraenone V in 1 ml of tetrahydrofuran are added dropwise to the mixture which has been cooled to −20° C. After 20 minutes, the mixture is poured onto water and extracted by shaking with petroleum ether, and the extract is dried on sodium sulfate. Column chromatography of the crude material over silica gel using 10% strength tert-butyl methyl ether in petroleum ether (40/60) gives 290 mg (67% yield) of (±)-periplanone A as a colorless oil ($R_f=0.5$).

We claim:

1. Substantially pure (±)-periplanone A having the structural formula:

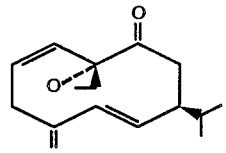

* * * * *